United States Patent [19]

Kordes et al.

[11] Patent Number: Plant 5,678

[45] Date of Patent: Mar. 4, 1986

[54] ROSE PLANT KORPERKI

[75] Inventors: Reimer Kordes; Werner Kordes; Hermann Kordes, all of Klein Offenseth-Sparrieshoop, Fed. Rep. of Germany

[73] Assignee: Jackson & Perkins Company, Medford, Oreg.

[21] Appl. No.: 651,520

[22] Filed: Sep. 17, 1984

[51] Int. Cl.[4] ..... A01H 5/00

[52] U.S. Cl. ..... Plt./21

[58] Field of Search ..... Plt./21

*Primary Examiner*—Robert E. Bagwill

*Attorney, Agent, or Firm*—Manford R. Haxton

[57] ABSTRACT

A hybrid tea rose variety having vigorous spreading, medium height plant, dark red buds and blooms with pointed petals, little fragrance, curled leaflets.

1 Drawing Figure

This present invention relates to a new and distinct variety of rose plant of the hybrid tea class which was originated by crossing an unnamed variety with the variety Uwe Seeler, non-patented.

The primary objective of this breeding was to produce a new rose variety of the hybrid tea class, suitable for garden use, bearing very double, red blooms on a strong, upright plant. This objective was substantially achieved along with other desirable improvements as evidenced by the following unique combination of characteristics which are outstanding in the new variety and which distinguish it from its parents as well as from all other varieties of which I am aware:

1. A vigorous, spreading plant, generally not as tall as varieties Mr. Lincoln, U.S. Plant Pat. No. 2,370, and American Pride, U.S. Plant Pat. No. 4,139;
2. Opening color of buds deep red with very little change throughout life of flower;
3. Little or no fragrance;
4. Leaflets that tend to curl upwards;
5. Medium-sized prickles, hooked sharply;
6. Quilling of petals causing them to appear pointed.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:
- *Seed parent.*—Unnamed variety.
- *Pollen parent.*—Uwe Seeler.

Classification:
- *Botanical.*—Rosa hybrid.
- *Commercial.*—Hybrid tea.

FLOWER

Observations made from specimens grown in a greenhouse at Irvine, Calif., in June.

Blooming habit: Continuous.

Bud:
- *Size.*—1¼" when petals start to unfurl.
- *Form.*—Short, blunt top.
- *Color.*—When sepals first divide, Near Red 46A; when half blown, upper side of petals Near Red 46A; lower side of petals Near Red 46C.
- *Sepals.*—Color: Green 138A. Three appendaged sepals lightly appendaged. Two appendaged sepals hairy edged.
- *Receptacle.*—Color: Green 138A. Shape: Funnel. Size: Medium, long, slender. Surface: Smooth.
- *Peduncle.*—Length: Short. Surface: Prickly and glandular. Color: Light green. Strength: Stiff, erect.
- *Opening.*—Petals fold out and edges curl causing petals to appear pointed.

Open bloom:
- *Size.*—Large. Average open size 4½".
- *Borne.*—Singly.
- *Stems.*—Long, strong.
- *Form.*—When first open, high center. Permanence: retains its form to the end; all petals curl, quill fashion.
- *Petalage.*—Number of petals under normal conditions: 50–55.
- *Color.*—Center of flower: Upper side of petals, Near Red 46A; reverse side of petals, Near Red 46C. Base of petals, Yellow-orange 16A when first opened — fades to white after three days. Major color: Red 46A.
- *Variegations.*—Usually shows white midribs on outer petals.
- *Discoloration.*—General tonality at end of first day: None. Third day: None.
- *Fragrance.*—None.

Petals:
- *Texture.*—Thick.
- *Shape.*—Round.
- *Form.*—Edges slightly quilled.
- *Arrangement.*—Imbricated. Petaloids in center, few.
- *Persistence.*—Drop off cleanly.
- *Lastingness.*—On the plant, long. As cut flower, long.

Reproductive parts:

*Anthers.*—Small. Color: Yellow. Arrangement: Regular around styles.
*Filaments.*—Color: Reddish with yellow base.
*Pollen.*—Gold yellow.
*Styles.*—Color: Red.
*Stigmas.*—Color: Yellow.

PLANT

Form: Bush.
Growth: Very vigorous, upright and spreading. Plant reaches 4½ to 5 feet under normal care at Irvine, Calif.
Foliage: Number of leaflets on normal mid-stem leaves: Usually 5.
*Size.*—Medium.
*Quantity.*—Normal.
*Color.*—New foliage: Greyed purple 187A. Old foliage: Dark green.
Leaflets:
*Shape.*—Oval, leaf edges tend to curl upwards.
*Texture.*—Glossy.
*Edge.*—Serrated.
*Serration.*—Single small.
*Petiole.*—Rachis: Color: Green to reddish. Underside: Prickles.

*Stipules.*—Long, bearded.
*Disease resistance.*—Slightly susceptible, resistant to mildew, under normal growing conditions at Irvine, Calif.
Wood:
*New wood.*—Color: Light green. Bark: Smooth.
*Old wood.*—Color: Green. Bark: Smooth.
Prickles:
*Quantity.*—On main canes from base: Ordinary. On laterals from main canes: Ordinary.
*Form.*—Medium, hooked downward.
*Color when young.*—Green to red.
Small prickles:
*Quantity.*—On main stalks, few. On laterals, few.
*Color.*—Brown.

I claim:

1. A new and distinct variety of rose plant of the hybrid tea class, substantially as herein shown and described, characterized particularly as to novelty by the unique combination of its vigorous spreading, medium height plant, dark red buds and blooms with pointed petals, little fragrance, curled leaflets.

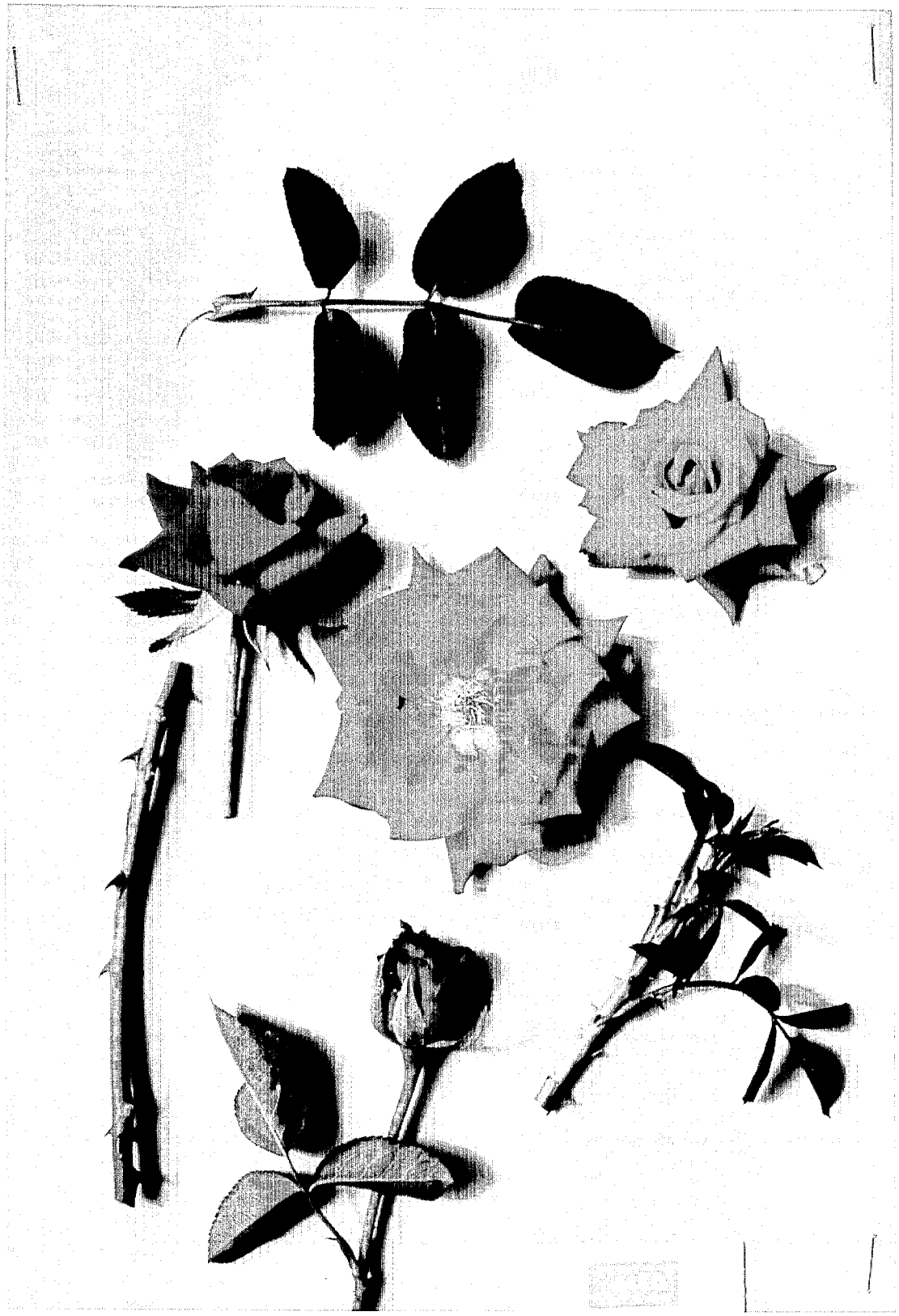

* * * * *